US012788877B2

(12) United States Patent
Kamrava et al.

(10) Patent No.: US 12,788,877 B2
(45) Date of Patent: Nov. 10, 2026

(54) CLUTCH DEVICE FOR COMPACT POSITIVE DISPLACEMENT PUMP OF A WEARABLE DRUG DELIVERY DEVICE

(71) Applicant: INSULET CORPORATION, Acton, MA (US)

(72) Inventors: Soroush Kamrava, Everett, MA (US); Daniel Allis, Boxford, MA (US); Jeffrey Barnes, Medford, MA (US)

(73) Assignee: INSULET CORPORATION, Acton, MA (US)

( * ) Notice: Subject to any disclaimer, the term of this patent is extended or adjusted under 35 U.S.C. 154(b) by 988 days.

(21) Appl. No.: 17/930,347

(22) Filed: Sep. 7, 2022

(65) Prior Publication Data

US 2023/0077167 A1 Mar. 9, 2023

Related U.S. Application Data

(60) Provisional application No. 63/241,633, filed on Sep. 8, 2021.

(51) Int. Cl.
*A61M 5/145* (2006.01)
*A61M 5/142* (2006.01)

(52) U.S. Cl.
CPC ...... *A61M 5/1452* (2013.01); *A61M 5/14244* (2013.01); *A61M 2005/14533* (2013.01)

(58) Field of Classification Search
CPC ...... A61M 2005/14533; A61M 5/1454; A61M 2005/3152; A61M 5/14244;
(Continued)

(56) References Cited

U.S. PATENT DOCUMENTS 1,441,508 A 1/1923 Jensen
2,198,666 A 4/1940 Gruskin
(Continued)

FOREIGN PATENT DOCUMENTS

CA 606281 A 10/1960
CN 1375338 A 10/2002
(Continued)

OTHER PUBLICATIONS

International Search Report and Written Opinion for International Application No. PCT/US2022/076051, mailed on Dec. 2, 2022, 14 pages.

(Continued)

*Primary Examiner* — Quynh-Nhu H. Vu
(74) *Attorney, Agent, or Firm* — Goodwin Procter LLP

(57) ABSTRACT

Embodiments of the present disclosure relate to techniques, processes, devices or systems for pump devices. In one approach, a wearable drug delivery device, may include a reservoir configured to store a fluid, the reservoir comprising a housing including an outer wall defining an interior chamber, and a drive mechanism for driving the fluid from the reservoir. The drive mechanism may include a plunger received in the interior chamber of the reservoir, a leadscrew extending from the plunger, and a clutch mechanism threadably engaged with the leadscrew, wherein the clutch mechanism is configured to allow the leadscrew to pass through the clutch mechanism when disengaged and is configured to grip the leadscrew when engaged such that the clutch mechanism rotates to advance the leadscrew and the plunger into the reservoir.

20 Claims, 8 Drawing Sheets

(58) Field of Classification Search

CPC ............ A61M 5/1452; A61M 5/14566; A61M 5/31501; A61M 5/31543

See application file for complete search history.

(56) References Cited

U.S. PATENT DOCUMENTS 2,459,972 A * 1/1949 Starkey .................. F16D 7/022 192/81 C
2,752,918 A 7/1956 Uytenbogaar
2,911,008 A 11/1959 Du Bois
3,111,822 A * 11/1963 Hansen .................. F16D 13/08 464/40
3,176,712 A 4/1965 Ramsden
3,297,260 A 1/1967 Barlow
3,464,359 A 9/1969 King
3,885,662 A 5/1975 Schaefer
3,946,732 A 3/1976 Hurscham
3,947,692 A 3/1976 Payne
3,993,061 A 11/1976 OLeary
4,108,177 A 8/1978 Pistor
4,152,098 A 5/1979 Moody et al.
4,210,173 A 7/1980 Choksi et al.
4,221,219 A 9/1980 Tucker
4,237,878 A 12/1980 Kobayashi et al.
4,257,324 A 3/1981 Stefansson et al.
4,268,150 A 5/1981 Chen
4,277,226 A 7/1981 Archibald
4,313,439 A 2/1982 Babb et al.
4,371,790 A 2/1983 Manning et al.
4,417,889 A 11/1983 Choi
4,424,720 A 1/1984 Bucchianeri
4,435,173 A 3/1984 Siposs et al.
4,475,905 A 10/1984 Himmelstrup
4,498,843 A 2/1985 Schneider et al.
4,507,115 A 3/1985 Kambara et al.
4,551,134 A 11/1985 Slavik et al.
4,562,751 A 1/1986 Nason et al.
4,567,549 A 1/1986 Lemme
4,585,439 A 4/1986 Michel
4,601,707 A 7/1986 Albisser et al.
4,634,427 A 1/1987 Hannula et al.
4,671,429 A 6/1987 Spaanderman et al.
4,678,408 A 7/1987 Nason et al.
4,684,368 A 8/1987 Kenyon
4,685,903 A 8/1987 Cable et al.
4,755,169 A 7/1988 Sarnoff et al.
4,766,889 A 8/1988 Trick et al.
4,808,161 A 2/1989 Kamen
4,846,797 A 7/1989 Howson et al.
4,858,619 A 8/1989 Toth
4,898,579 A 2/1990 Groshong et al.
4,908,017 A 3/1990 Howson et al.
4,944,659 A 7/1990 Labbe et al.
4,969,874 A 11/1990 Michel et al.
4,991,743 A 2/1991 Walker
5,007,458 A 4/1991 Marcus et al.
5,020,325 A 6/1991 Henault
5,062,841 A 11/1991 Siegel
5,135,485 A 8/1992 Cohen et al.
5,147,311 A 9/1992 Pickhard
5,178,609 A 1/1993 Ishikawa
5,205,819 A 4/1993 Ross et al.
5,213,483 A 5/1993 Flaherty et al.
5,222,362 A 6/1993 Maus et al.
5,236,416 A 8/1993 McDaniel et al.
5,261,882 A 11/1993 Sealfon
5,261,884 A 11/1993 Stern et al.
5,277,338 A 1/1994 Divall et al.
5,281,202 A 1/1994 Weber et al.
5,346,476 A 9/1994 Elson
5,364,342 A 11/1994 Beuchat et al.
5,388,615 A 2/1995 Edlund et al.
5,433,710 A 7/1995 VanAntwerp et al.
5,503,628 A 4/1996 Fetters et al.
5,520,661 A 5/1996 Lal et al.
5,533,389 A 7/1996 Kamen et al.
5,575,770 A 11/1996 Melsky et al.
5,582,593 A 12/1996 Hultman
5,618,269 A 4/1997 Jacobsen et al.
5,628,309 A 5/1997 Brown
5,637,095 A 6/1997 Nason et al.
5,665,070 A 9/1997 McPhee
5,713,875 A 2/1998 Tanner, II
5,747,350 A 5/1998 Sattler
5,748,827 A 5/1998 Holl et al.
5,776,103 A 7/1998 Kriesel et al.
5,779,676 A 7/1998 Kriesel et al.
5,785,688 A 7/1998 Joshi et al.
5,797,881 A 8/1998 Gadot
5,800,397 A 9/1998 Wilson et al.
5,807,075 A 9/1998 Jacobsen et al.
5,814,020 A 9/1998 Gross
5,839,467 A 11/1998 Saaski et al.
5,876,377 A 3/1999 Kriesel
5,891,097 A 4/1999 Saito et al.
5,897,530 A 4/1999 Jackson
5,906,597 A 5/1999 McPhee
5,911,716 A 6/1999 Rake et al.
5,919,167 A 7/1999 Mulhauser et al.
5,957,890 A 9/1999 Mann et al.
5,961,492 A 10/1999 Kriesel et al.
5,971,963 A 10/1999 Choi
6,019,747 A 2/2000 McPhee
6,045,533 A 4/2000 Kriesel et al.
6,050,457 A 4/2000 Arnold et al.
6,068,615 A 5/2000 Brown et al.
6,152,898 A 11/2000 Olsen
6,159,188 A 12/2000 Laibovitz et al.
6,174,300 B1 1/2001 Kriesel et al.
6,190,359 B1 2/2001 Heruth
6,200,293 B1 3/2001 Kriesel et al.
6,206,850 B1 3/2001 ONeil
6,210,368 B1 4/2001 Rogers
6,352,522 B1 3/2002 Kim et al.
6,363,609 B1 4/2002 Pickren
6,375,638 B2 4/2002 Nason et al.
6,474,219 B2 11/2002 Klitmose et al.
6,485,461 B1 11/2002 Mason et al.
6,485,462 B1 11/2002 Kriesel
6,488,652 B1 12/2002 Weijand et al.
6,520,936 B1 2/2003 Mann
6,527,744 B1 3/2003 Kriesel et al.
6,537,249 B2 3/2003 Kriesell et al.
6,539,286 B1 3/2003 Jiang
6,569,115 B1 5/2003 Barker et al.
6,595,956 B1 7/2003 Gross et al.
6,656,158 B2 12/2003 Mahoney et al.
6,666,852 B2 12/2003 Niedospial, Jr.
6,699,218 B2 3/2004 Flaherty et al.
6,723,072 B2 4/2004 Flaherty et al.
6,740,059 B2 5/2004 Flaherty
6,749,407 B2 6/2004 Xie et al.
6,851,260 B2 2/2005 Mernoe
6,883,778 B1 4/2005 Newton et al.
7,018,360 B2 3/2006 Flaherty et al.
7,104,275 B2 9/2006 Dille
7,128,727 B2 10/2006 Flaherty et al.
7,137,964 B2 11/2006 Flaherty
7,160,272 B1 1/2007 Eyal et al.
7,220,245 B2 5/2007 Kriesel
7,303,549 B2 12/2007 Flaherty
7,771,392 B2 8/2010 De Polo et al.
7,914,499 B2 3/2011 Gonnelli et al.
7,951,114 B2 5/2011 Rush et al.
8,267,921 B2 9/2012 Yodfat et al.
8,382,703 B1 2/2013 Abdelaal
8,499,913 B2 8/2013 Gunter
8,613,724 B2 12/2013 Lanier, Jr. et al.
8,758,308 B2 6/2014 Alferness et al.
8,905,995 B2 12/2014 Mernoe
8,920,376 B2 12/2014 Caffey et al.
8,939,935 B2 1/2015 OConnor et al.
9,180,244 B2 11/2015 Anderson et al.
9,192,716 B2 11/2015 Jugl et al.

(56) References Cited

U.S. PATENT DOCUMENTS

| | | | | |
|---|---|---|---|---|
| 9,402,950 | B2 | 8/2016 | Dilanni et al. | |
| 9,539,596 | B2 | 1/2017 | Ikushima | |
| 9,675,760 | B2 * | 6/2017 | Butler | A61M 5/3155 |
| 10,420,883 | B2 * | 9/2019 | Diianni | A61M 5/14248 |
| 10,441,723 | B2 | 10/2019 | Nazzaro | |
| 10,695,485 | B2 | 6/2020 | Nazzaro | |
| 11,229,741 | B2 * | 1/2022 | Diianni | F04B 9/02 |
| 12,329,928 | B2 * | 6/2025 | Diianni | A61M 5/158 |
| 2001/0016710 | A1 | 8/2001 | Nason et al. | |
| 2001/0034502 | A1 | 10/2001 | Moberg et al. | |
| 2001/0056258 | A1 | 12/2001 | Evans | |
| 2002/0029018 | A1 | 3/2002 | Jeffrey | |
| 2002/0032374 | A1 | 3/2002 | Holker et al. | |
| 2002/0037221 | A1 | 3/2002 | Mastrangelo et al. | |
| 2002/0066715 | A1 | 6/2002 | Niedospial | |
| 2002/0173769 | A1 | 11/2002 | Gray et al. | |
| 2002/0173830 | A1 | 11/2002 | Starkweather et al. | |
| 2003/0040715 | A1 | 2/2003 | DAntonio et al. | |
| 2003/0055380 | A1 | 3/2003 | Flaherty | |
| 2003/0097092 | A1 | 5/2003 | Flaherty | |
| 2003/0109827 | A1 | 6/2003 | Lavi et al. | |
| 2003/0120262 | A1 | 6/2003 | Weiland et al. | |
| 2003/0136189 | A1 | 7/2003 | Lauman et al. | |
| 2003/0139774 | A1 | 7/2003 | Epstein et al. | |
| 2003/0163097 | A1 | 8/2003 | Fleury et al. | |
| 2003/0198558 | A1 | 10/2003 | Nason et al. | |
| 2003/0199825 | A1 | 10/2003 | Flaherty | |
| 2004/0010207 | A1 | 1/2004 | Flaherty et al. | |
| 2004/0064088 | A1 | 4/2004 | Gorman et al. | |
| 2004/0068224 | A1 | 4/2004 | Couvillon, Jr. et al. | |
| 2004/0069044 | A1 | 4/2004 | Lavi et al. | |
| 2004/0092865 | A1 | 5/2004 | Flaherty et al. | |
| 2004/0094733 | A1 | 5/2004 | Hower et al. | |
| 2004/0122361 | A1 | 6/2004 | Hart et al. | |
| 2004/0153032 | A1 | 8/2004 | Garribotto et al. | |
| 2005/0020980 | A1 | 1/2005 | Inoue et al. | |
| 2005/0165363 | A1 | 7/2005 | Judson et al. | |
| 2005/0203461 | A1 | 9/2005 | Flaherty et al. | |
| 2005/0238507 | A1 * | 10/2005 | Dilanni | F04B 9/08 417/415 |
| 2005/0273059 | A1 | 12/2005 | Mernoe | |
| 2005/0277882 | A1 | 12/2005 | Kriesel | |
| 2006/0041229 | A1 | 2/2006 | Garibotto et al. | |
| 2006/0079765 | A1 | 4/2006 | Neer et al. | |
| 2006/0155210 | A1 | 7/2006 | Beckman et al. | |
| 2006/0173439 | A1 | 8/2006 | Thorne et al. | |
| 2006/0178633 | A1 | 8/2006 | Garibotto et al. | |
| 2006/0253085 | A1 | 11/2006 | Geismar et al. | |
| 2006/0253088 | A1 | 11/2006 | Chow et al. | |
| 2006/0282290 | A1 | 12/2006 | Flaherty et al. | |
| 2007/0005018 | A1 | 1/2007 | Tekbuchava | |
| 2007/0025811 | A1 | 2/2007 | Wilhelm | |
| 2007/0073236 | A1 | 3/2007 | Merno et al. | |
| 2007/0088271 | A1 | 4/2007 | Richards | |
| 2007/0112332 | A1 | 5/2007 | Harding et al. | |
| 2007/0118405 | A1 | 5/2007 | Campbell et al. | |
| 2007/0282269 | A1 | 12/2007 | Carter et al. | |
| 2008/0001737 | A1 | 1/2008 | Metry | |
| 2008/0004515 | A1 | 1/2008 | Jennewine | |
| 2008/0051738 | A1 | 2/2008 | Griffin | |
| 2008/0051765 | A1 | 2/2008 | Mounce | |
| 2008/0065000 | A1 | 3/2008 | Bidinger et al. | |
| 2008/0114304 | A1 | 5/2008 | Nalesso et al. | |
| 2008/0119790 | A1 | 5/2008 | Hawkins et al. | |
| 2008/0172028 | A1 | 7/2008 | Blomquist | |
| 2008/0243211 | A1 | 10/2008 | Cartwright et al. | |
| 2008/0249508 | A1 | 10/2008 | Lopez et al. | |
| 2008/0294040 | A1 | 11/2008 | Mohiuddin et al. | |
| 2009/0024083 | A1 | 1/2009 | Kriesel et al. | |
| 2009/0062767 | A1 | 3/2009 | Van Antwerp et al. | |
| 2009/0198215 | A1 | 8/2009 | Chong et al. | |
| 2009/0278875 | A1 | 11/2009 | Holm et al. | |
| 2009/0326472 | A1 | 12/2009 | Carter et al. | |
| 2010/0036326 | A1 | 2/2010 | Matusch | |
| 2010/0152658 | A1 | 6/2010 | Hanson et al. | |
| 2010/0241066 | A1 | 9/2010 | Hansen et al. | |
| 2011/0054399 | A1 | 3/2011 | Chong et al. | |
| 2011/0073620 | A1 | 3/2011 | Verrilli | |
| 2011/0130742 | A1 | 6/2011 | Hawkins et al. | |
| 2011/0144586 | A1 | 6/2011 | Michaud et al. | |
| 2011/0180480 | A1 | 7/2011 | Kloeffel et al. | |
| 2011/0230833 | A1 | 9/2011 | Landman et al. | |
| 2011/0231204 | A1 | 9/2011 | De La Huerga | |
| 2012/0056000 | A1 | 3/2012 | Shores | |
| 2012/0078161 | A1 | 3/2012 | Masterson et al. | |
| 2012/0172817 | A1 | 7/2012 | Bruggemann et al. | |
| 2012/0209207 | A1 | 8/2012 | Gray et al. | |
| 2013/0006213 | A1 | 1/2013 | Arnitz et al. | |
| 2013/0017099 | A1 | 1/2013 | Genoud | |
| 2013/0064701 | A1 | 3/2013 | Konishi | |
| 2013/0177455 | A1 | 7/2013 | Kamen et al. | |
| 2013/0178803 | A1 * | 7/2013 | Raab | A61M 5/31585 604/211 |
| 2013/0245545 | A1 | 9/2013 | Arnold et al. | |
| 2013/0267932 | A1 | 10/2013 | Franke et al. | |
| 2013/0296792 | A1 | 11/2013 | Cabiri | |
| 2014/0018730 | A1 | 1/2014 | Muller-Pathle | |
| 2014/0127048 | A1 | 5/2014 | Dilanni et al. | |
| 2014/0128839 | A1 | 5/2014 | Dilanni et al. | |
| 2014/0142508 | A1 | 5/2014 | Dilanni et al. | |
| 2014/0148784 | A1 | 5/2014 | Anderson et al. | |
| 2014/0171901 | A1 | 6/2014 | Langsdorf et al. | |
| 2015/0041498 | A1 | 2/2015 | Kakiuchi et al. | |
| 2015/0051487 | A1 | 2/2015 | Uber et al. | |
| 2015/0057613 | A1 | 2/2015 | Clemente et al. | |
| 2015/0064036 | A1 | 3/2015 | Eberhard | |
| 2015/0137017 | A1 | 5/2015 | Ambrosina et al. | |
| 2015/0157537 | A1 | 6/2015 | Lanigan et al. | |
| 2015/0202386 | A1 | 7/2015 | Brady et al. | |
| 2015/0290389 | A1 | 10/2015 | Nessel | |
| 2015/0297825 | A1 | 10/2015 | Focht et al. | |
| 2016/0008536 | A1 | 1/2016 | Gravesen et al. | |
| 2016/0008549 | A1 | 1/2016 | Plumptre et al. | |
| 2016/0025544 | A1 | 1/2016 | Kamen | |
| 2016/0055842 | A1 | 2/2016 | Defranks et al. | |
| 2016/0082242 | A1 | 3/2016 | Burton et al. | |
| 2016/0129190 | A1 | 5/2016 | Haitsuka | |
| 2016/0144105 | A1 | 5/2016 | Hooven et al. | |
| 2016/0193423 | A1 | 7/2016 | Bilton | |
| 2016/0213851 | A1 | 7/2016 | Weibel et al. | |
| 2016/0296695 | A1 | 10/2016 | Hassman et al. | |
| 2017/0021096 | A1 | 1/2017 | Cole et al. | |
| 2017/0021137 | A1 | 1/2017 | Cole | |
| 2017/0100541 | A1 | 4/2017 | Constantineau et al. | |
| 2017/0128664 | A1 * | 5/2017 | Diianni | A61M 5/158 |
| 2017/0216516 | A1 | 8/2017 | Dale | |
| 2017/0239415 | A1 | 8/2017 | Hwang et al. | |
| 2017/0290975 | A1 | 10/2017 | Barmaimon et al. | |
| 2017/0340811 | A1 | 11/2017 | Pananen | |
| 2018/0008767 | A1 | 1/2018 | Lambert | |
| 2018/0021521 | A1 | 1/2018 | Sanchez | |
| 2018/0185579 | A1 | 7/2018 | Joseph et al. | |
| 2018/0313346 | A1 | 11/2018 | Oakes | |
| 2019/0001057 | A1 | 1/2019 | Tsoukalis et al. | |
| 2019/0192782 | A1 | 6/2019 | Pedersen et al. | |
| 2019/0365993 | A1 | 12/2019 | Staub et al. | |
| 2020/0009315 | A1 | 1/2020 | Brouet et al. | |
| 2020/0345931 | A1 | 11/2020 | Gray et al. | |

FOREIGN PATENT DOCUMENTS

| | | | |
|---|---|---|---|
| CN | 102498292 | B | 7/2015 |
| CN | 204972511 | U | 1/2016 |
| CN | 105764543 | B | 7/2016 |
| CN | 206175149 | U | 5/2017 |
| CN | 107096091 | A | 8/2017 |
| CN | 108472441 | A | 8/2018 |
| DE | 4200595 | A1 | 7/1993 |
| DE | 19723648 | C1 | 8/1998 |
| DE | 102005040344 | A1 | 3/2007 |
| EP | 0454331 | A1 | 10/1991 |
| EP | 0789146 | A1 | 8/1997 |
| EP | 867196 | A2 | 9/1998 |
| EP | 1065378 | A2 | 1/2001 |

(56) References Cited

FOREIGN PATENT DOCUMENTS

| | | | |
|---|---|---|---|
| EP | 1177802 | A1 | 2/2002 |
| EP | 1403519 | A1 | 3/2004 |
| EP | 2397181 | A1 | 12/2011 |
| EP | 2468338 | A1 | 6/2012 |
| EP | 2703024 | A1 | 3/2014 |
| EP | 1874390 | B1 | 10/2014 |
| EP | 2830499 | A1 | 2/2015 |
| FR | 2096275 | A5 | 2/1972 |
| FR | 2455269 | A1 | 11/1980 |
| FR | 2507637 | A1 | 12/1982 |
| FR | 2731475 | A1 | 9/1996 |
| GB | 357139 | A | 9/1931 |
| GB | 810488 | A | 3/1959 |
| GB | 875034 | A | 8/1961 |
| GB | 1204836 | A | 9/1970 |
| GB | 2008806 | A | 6/1979 |
| GB | 2077367 | A | 12/1981 |
| GB | 2456681 | A | 7/2009 |
| GB | 2549750 | A | 11/2017 |
| IL | 46017 | A | 11/1977 |
| JP | S58083969 | A | 5/1983 |
| JP | 06063133 | A | 3/1994 |
| JP | H06296690 | A | 10/1994 |
| JP | H08238324 | A | 9/1996 |
| JP | 2004247271 | A | 9/2004 |
| JP | 2004274719 | A | 9/2004 |
| JP | 2005188355 | A | 7/2005 |
| JP | 2006159228 | A | 6/2006 |
| JP | 6098988 | B2 | 9/2006 |
| JP | 2006249130 | A | 9/2006 |
| JP | 2008536625 | A | 9/2008 |
| JP | 2009514580 | A | 4/2009 |
| JP | 2010510027 | A | 4/2010 |
| JP | 2014-519388 | A | 8/2014 |
| JP | 2017513577 | A | 6/2017 |
| KR | 1020210040712 | A | 4/2021 |
| NL | 1019126 | C1 | 4/2003 |
| WO | 8101658 | A1 | 6/1981 |
| WO | 8606796 | A1 | 11/1986 |
| WO | 9320864 | A1 | 10/1993 |
| WO | 9415660 | A1 | 7/1994 |
| WO | 9855073 | A1 | 12/1998 |
| WO | 9856293 | A1 | 12/1998 |
| WO | 9910040 | A1 | 3/1999 |
| WO | 9910049 | A1 | 3/1999 |
| WO | 9962576 | A1 | 12/1999 |
| WO | 0029047 | A1 | 5/2000 |
| WO | 0178812 | A1 | 10/2001 |
| WO | 0220073 | A2 | 3/2002 |
| WO | 0226282 | A2 | 4/2002 |
| WO | 2002076535 | A1 | 4/2002 |
| WO | 2003097133 | A1 | 4/2002 |
| WO | 02068823 | A1 | 9/2002 |
| WO | 2004032994 | A2 | 4/2004 |
| WO | 2004056412 | A2 | 7/2004 |
| WO | 2004110526 | A1 | 12/2004 |
| WO | 2007066152 | A2 | 6/2007 |
| WO | 2008133702 | A1 | 11/2008 |
| WO | 2009039203 | A2 | 3/2009 |
| WO | 2009070731 | A1 | 6/2009 |
| WO | 2009141005 | A1 | 11/2009 |
| WO | 2010022069 | A2 | 2/2010 |
| WO | 2010077279 | A1 | 7/2010 |
| WO | 2010139793 | A1 | 12/2010 |
| WO | 2011010198 | A2 | 1/2011 |
| WO | 2011031458 | A1 | 3/2011 |
| WO | 2011069935 | A2 | 6/2011 |
| WO | 2011075042 | A1 | 6/2011 |
| WO | 2011133823 | A1 | 10/2011 |
| WO | 2012073032 | A1 | 6/2012 |
| WO | 2013050535 | A2 | 4/2013 |
| WO | 2013137893 | A1 | 9/2013 |
| WO | 2013149186 | A1 | 10/2013 |
| WO | 2014029416 | A1 | 2/2014 |
| WO | 2014149357 | A1 | 9/2014 |
| WO | 2014154777 | A1 | 10/2014 |
| WO | 2014179774 | A1 | 11/2014 |
| WO | 2014204894 | A2 | 12/2014 |
| WO | 2015032772 | A1 | 3/2015 |
| WO | 2015048791 | A1 | 4/2015 |
| WO | 2015061690 | A1 | 4/2015 |
| WO | 2015081337 | A2 | 6/2015 |
| WO | 2015117854 | A1 | 8/2015 |
| WO | 2015167201 | A1 | 11/2015 |
| WO | 2015177082 | A1 | 11/2015 |
| WO | 2015177652 | A1 | 11/2015 |
| WO | 2016162755 | A2 | 10/2016 |
| WO | 2017148855 | A1 | 9/2017 |
| WO | 2017187177 | A1 | 11/2017 |
| WO | 2021016452 | A1 | 1/2021 |

OTHER PUBLICATIONS

European Search Report and Written Opinion for European Patent Application No. EP20174878, dated Sep. 29, 2020, 8 pages.

Schott web-page image from Jul. 9, 2016, https://www.us.schott.com/pharmaceutical_packaging/english/products/cartridges.html.

International Search Report and Written Opinion for International Patent Application No. PCT/US2021/055581, dated Feb. 8, 2022, 19 pages.

International Search Report and Written Opinion for International Patent Application No. PCT/US2022/011356, dated Apr. 29, 2022, 19 pages.

International Search Report and Written Opinion for PCT/US2018/014351, mailed on Jun. 4, 2018, 9 pages.

Lind et al. "Linear Motion Miniature Actuators." Paper presented at the 2nd Tampere International Conference on Machine Automation, Tampere, Finland (Sep. 1998).

Author Unknown "The Animas R-1000 Insulin Pump—Animas Corporation intends to exit the insulin pump businessand discontinue the manufacturing and sale of Animas® Vibe® and One Touch Ping® insulin pumps." [online], Dec. 1999 [retrieved on Jan. 8, 2019]. Retrieved from the Internet URL: http://www.animaspatientsupport.com/.

Author Unknown, CeramTec "Discover the Electro Ceramic Products CeramTec acquired from Morgan AdvancedMaterials" [online], Mar. 1, 2001 [retrieved on Jan. 8, 2019. Retrieved from the Internet URL: http://www.morgantechnicalceramics.com/.

Vaughan, M.E., "The Design, Fabrication, and Modeling of a Piezoelectric Linear Motor." Master's thesis, Virginia Polytechnic Institute and State University, VA. (2001).

Galante et al., "Design, Modeling, and Performance of a High Force Piezoelectric Inchworm Motor," Journal of Intelligent Material Systems and Structures, vol. 10, 962 -972 (1999).

International Search Report and Written Opinion for International Application No. PCT/US2017/055054, mailed on Jan. 25, 2018, 13 pages.

International Search Report and Written Opinion for International Application No. PCT/US2018/045155, mailed on Oct. 15, 2018, 15 pages.

International Preliminary Report on Patentability for International Application No. PCT/US2017/034811 issued on Nov. 27, 2018, 10 pages.

International Preliminary Report on Patentability for International Patent Application No. PCT/US2017/046508, Feb. 12, 2019, 10 pages.

International Search Report and Written Opinion for International Application No. PCT/US2017/046508, mailed on Jan. 17, 2018, 14 pages.

International Search Report and Written Opinion for International Application No. PCT/US2017/046777, mailed on Dec. 13, 2017, 14 pages.

International Search Report and Written Opinion for International Application No. PCT/US2017/046737, mailed on Dec. 14, 2017, 11 pages.

International Search Report and Written Opinion for International Application No. PCT/US2017/034814, mailed on Oct. 11, 2017, 18 pages.

(56) References Cited

OTHER PUBLICATIONS

European Search Report and Written Opinion for the European Patent Application No. EP19177571, dated Oct. 30, 2019, 8 pages.
International Preliminary Report on Patentability for International Patent Application No. PCT/US2018/014351, dated Jul. 23, 2019, 7 pages.
International Preliminary Report on Patentability for International Patent Application No. PCT/US2017/046777, dated Feb. 19, 2019, 8 pages.
International Preliminary Report on Patentability for International Patent Application No. PCT/US2017/046737, dated Feb. 19, 2019, 8 pages.
International Preliminary Report on Patentability for International Patent Application No. PCT/US2017/055054, dated Apr. 9, 2019, 8 pages.
International Search Report and Written Opinion for Application No. PCT/US2017/034811, mailed Oct. 18, 2017, 15 pages.
EPO Search Report received in Application No. 13768938.6, dated Nov. 11, 2015, 8 pages.
International Search Report and Written Opinion for PCT Application No. PCT/US13/34674, mailed Aug. 6, 2013, 17 pages.
International Search Report and Written Opinion for International Application No. PCT/GB2007/004073, Jan. 31, 2008, 8 pages.
International Search Report and Written Opinion for International Patent Application No. PCT/US2019/063615, dated May 3, 2020, 17 pages.
International Preliminary Report on Patentability for International Patent Application No. PCT/US2018/045155, dated Feb. 14, 2020, 10 pages.
International Search Report and Written Opinion for International Patent Application No. PCT/US2019/035756, dated Jul. 31, 2019, 11 pages.
International Search Report and Written Opinion for PCT Application No. PCT/US2019/059854, mailed Aug. 26, 2020, 15 pages.
International Search Report and Written Opinion, Application No. PCT/US2022/016713, mailed Aug. 5, 2022, 19 pages.
International Search Report and Written Opinion for International Patent Application No. PCT/US2022/029012, mailed Aug. 19, 2022, 12 pages.
European Search Report and Written Opinion for the EP Application No. EP17736272, dated Oct. 7, 2019.
International Search Report and Written Opinion dated Feb. 13, 2009 issued in related International Patent Application No. PCT/US08/84971, 6 pages.
NovoLog, "NovoLog Flex Pen", available at http://www.novolog.com/devices-flexpen.asp; retrieved on Sep. 11, 2007.
International Search Report and Written Opinion dated Mar. 27, 2020 issued in International Patent Application No. PCT/US19/42408, 18 pages.
International Search Report and Written Opinion for Application No. PCT/US17/12207, mailed May 26, 2017, 10 pages.

* cited by examiner

CLUTCH DEVICE FOR COMPACT POSITIVE DISPLACEMENT PUMP OF A WEARABLE DRUG DELIVERY DEVICE

RELATED APPLICATIONS

This application claims the benefit of U.S. Provisional Patent Application No. 63/241,633, filed Sep. 8, 2021, the contents of which are incorporated herein by reference in their entirety.

TECHNICAL FIELD

The disclosed embodiments generally relate to medication delivery. More particularly, the disclosed embodiments relate to techniques, processes, systems, and dispensing devices for delivering a fluid medicament in a space-efficient manner.

BACKGROUND

Fluid delivery devices have numerous uses such as delivering a fluid medicament to a patient subcutaneously. In a patient with diabetes mellitus, for example, ambulatory infusion pumps have been used to deliver insulin to the patient. These infusion pumps have the ability to offer sophisticated fluid delivery profiles including variable basal rates and bolus requirements. The ability to carefully control drug delivery can result in better efficacy of the drug and therapy and less toxicity to the patient.

Some existing infusion pumps include a reservoir to contain the fluid medicament and use electromechanical pumping or metering technology to deliver the fluid medicament via tubing to a needle and/or soft cannula that is inserted subcutaneously into the patient. Some infusion pumps have been designed to be relatively small, low cost, light-weight, and easy-to-use. These pumps include insertion mechanisms for delivering the needle and/or soft cannula into a patient. The design of the insertion mechanism may be improved, however, to reduce the size of the pump, to improve the comfort to the user, and/or to reduce the number of components of the pump.

Accordingly, there is a need for a simplified system for accurately expelling fluid medicament from a reservoir, which also reduces overall drug delivery device size.

SUMMARY

This Summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

In some approaches, a wearable drug delivery device may include a reservoir configured to store a fluid, the reservoir comprising a housing including an outer wall defining an interior chamber, and a drive mechanism for driving the fluid from the reservoir. The drive mechanism may include a plunger received in the interior chamber of the reservoir, a leadscrew extending from the plunger, and a clutch mechanism threadably engaged with the leadscrew, wherein the clutch mechanism is configured to allow the leadscrew to pass through the clutch mechanism when disengaged and is configured to grip the leadscrew when engaged such that the clutch mechanism rotates to advance the leadscrew and the plunger in the reservoir.

In some approaches, a wearable drug delivery device may include a reservoir configured to store a liquid drug, the reservoir comprising a housing including an outer wall defining an interior chamber, and a drive mechanism for driving the liquid drug from the reservoir. The drive mechanism may include a plunger received in the interior chamber of the reservoir, a leadscrew extending from the plunger, and a drive wheel operable with a clutch mechanism to rotate a clutch spring to advance the leadscrew, wherein the clutch mechanism is configured to allow the leadscrew to pass through the clutch spring when in a disengaged position and is configured to grip the leadscrew when in an engaged position such that the drive wheel rotates the clutch spring to advance the leadscrew and the plunger into the reservoir.

In some approaches, a method may include providing a reservoir configured to store a liquid drug, the reservoir comprising a housing including an outer wall defining an interior chamber, and providing a drive mechanism for driving the liquid drug from the reservoir. The drive mechanism may include a plunger received in the interior chamber of the reservoir, a leadscrew extending from the plunger, and a drive wheel operable with a clutch mechanism. The method may further include rotating a clutch spring of the clutch mechanism to advance the leadscrew, wherein the clutch mechanism is configured to allow the leadscrew to pass through the clutch spring when in a disengaged position and configured to grip the leadscrew when in an engaged position.

BRIEF DESCRIPTION OF THE DRAWINGS

In the drawings, like reference characters generally refer to the same parts throughout the different views. In the following description, various embodiments of the present disclosure are described with reference to the following drawings, in which.

Figure 1:
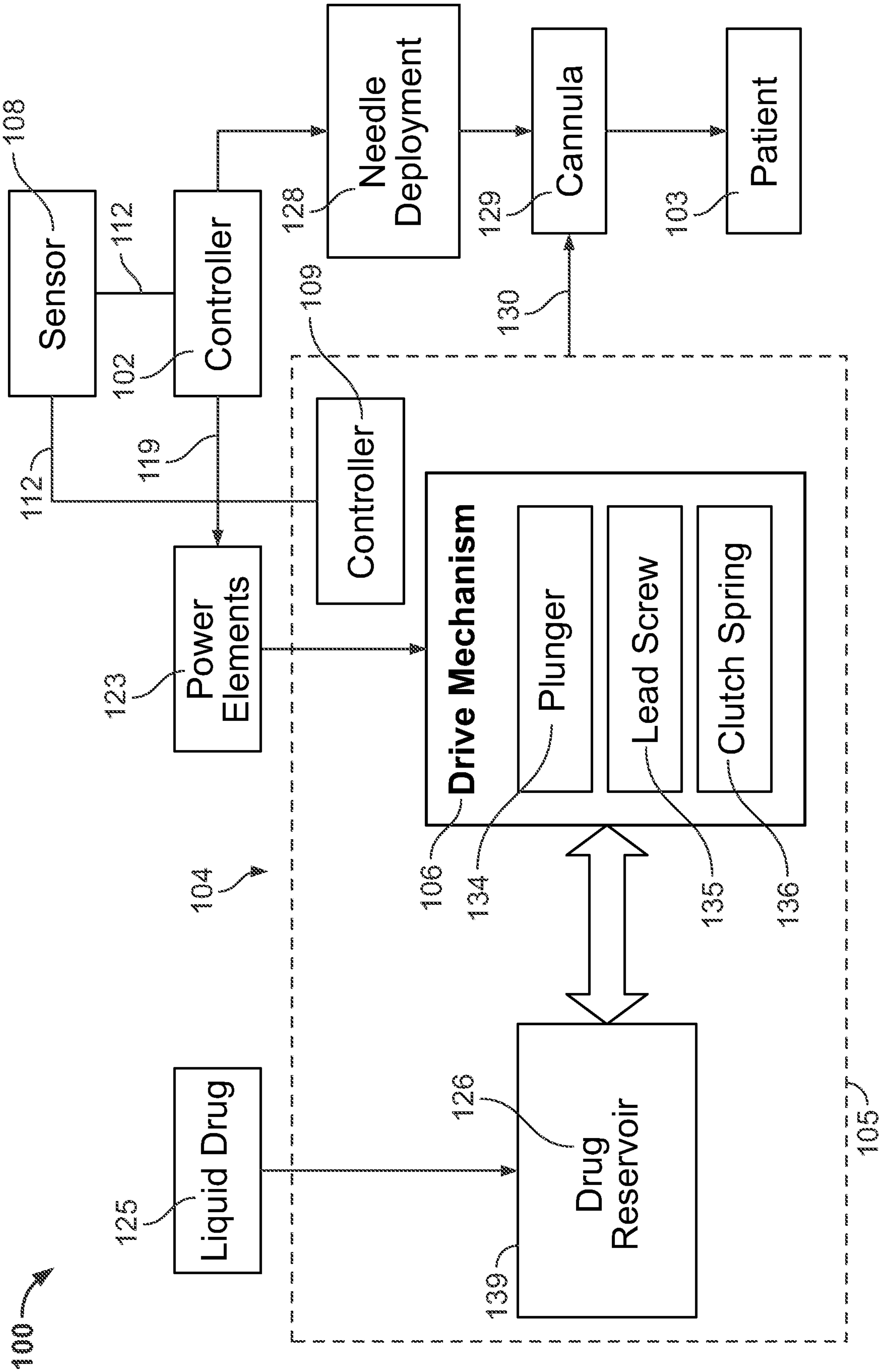
FIG. 1 illustrates a schematic diagram of a drug delivery system according to embodiments of the present disclosure.

The drawings are not necessarily to scale. The drawings are merely representations, not intended to portray specific parameters of the disclosure. The drawings are intended to depict exemplary embodiments of the disclosure, and therefore are not be considered as limiting in scope. Furthermore, certain elements in some of the figures may be omitted, or illustrated not-to-scale, for illustrative clarity. Still furthermore, for clarity, some reference numbers may be omitted in certain drawings.

DETAILED DESCRIPTION

Systems, devices, and methods in accordance with the present disclosure will now be described more fully hereinafter with reference to the accompanying drawings, where one or more embodiments are shown. The systems, devices, and methods may be embodied in many different forms and are not to be construed as being limited to the embodiments set forth herein. Instead, these embodiments are provided so the disclosure will be thorough and complete, and will fully convey the scope of methods and devices to those skilled in the art. Each of the systems, devices, and methods disclosed herein provides one or more advantages over conventional systems, components, and methods.

One approach for actuating a fluidic pump is to employ a linear motion generated by a leadscrew and a spring/clutch mechanism. This mechanism converts the rotational motion of an actuator, which may be one or more SMA wires, solenoids, motors, etc., to an accurate linear motion. As an example, in a positive displacement fluidic pump, the linear motion generated by the leadscrew is transferred to a plunger within a reservoir and results in an accurate and controlled dispensing of the fluid from the reservoir. During the filling process, the plunger remains disengaged from the leadscrew and the spring/clutch mechanism so the fluid may move the plunger freely to any position based the filled volume. When the user is done filling, the spring/clutch mechanism connects with the leadscrew and the plunger, thus enabling the device to dispense the fluid out of the reservoir.

In some embodiments, the spring is initially in the loaded configuration with an inside diameter (ID) larger than the outside diameter (OD) of the leadscrew, thus allowing the spring and the leadscrew to move freely relative to one another as the user fills the pod. When desired, the clutch mechanism may release the spring, which causes a reduction in the ID of the coil and direct engagement of the spring with the leadscrew. In some embodiments, the spring engages with threading along an exterior of the leadscrew. Rotation of the leadscrew therefore results in the linear motion of the spring and the plunger, enabling the pod to accurately dispense the fluid.

In various embodiments, the wearable drug delivery device described herein may include an analyte sensor, such as a blood glucose sensor, and the cannula or microneedle array may be operable in allowing the device to measure an analyte level in a user of the device.

FIG. 1 illustrates a simplified block diagram of an example system (hereinafter "system") 100. The system 100 may be a wearable or on-body drug delivery device and/or an analyte sensor attached to the skin of a patient 103. The system 100 may include a controller 102, a pump mechanism 104 (hereinafter "pump 104"), and a sensor 108 within one or more housings. The sensor 108 may be a glucose or other analyte monitor such as, for example, a continuous glucose monitor, and may be incorporated into the wearable device. The sensor 108 may, for example, be operable to measure blood glucose (BG) values of a user to generate a measured BG level signal 112. The controller 102, the pump 104, and the sensor 108 may be communicatively coupled to one another via a wired or wireless communication path. For example, each of the controller 102, the pump 104 and the sensor 108 may be equipped with a wireless radio frequency transceiver operable to communicate via one or more communication protocols, such as Bluetooth®, or the like. The system 100 may also include a delivery pump device (hereinafter "device") 105, which includes a drive mechanism 106 coupled to a reservoir 126 for driving a liquid drug 125 therefrom. As will be described in greater detail herein, the drive mechanism 106 may include a piston head or plunger 134 disposed within an interior chamber of a housing 139 of the reservoir 126, and a leadscrew 135 couplable with a clutch spring 136. The system 100 may include additional components which are not shown or described for the sake of brevity.

The controller 102 may receive a desired BG level signal, which may be a first signal, indicating a desired BG level or range for the patient 103. The desired BG level signal may be stored in memory of a controller 109 on device 105, received from a user interface to the controller 102, or another device, or by an algorithm within controller 109 (or controller 102) that automatically determines an appropriate BG level or target for the patient 103. The sensor 108 may be coupled to the patient 103 and operable to measure an approximate value of a BG level of the user. In response to the measured BG level or value, the sensor 108 may generate a signal indicating the measured BG value. As shown, the controller 102 may also receive from the sensor 108 via a communication path, the measured BG level signal 112, which may be a second signal.

Based on the desired BG level signal and the measured BG level signal 112, the controller 102 or controller 109 may generate one or more control signals for directing operation of the pump 104. For example, one control signal 119 from the controller 102 or controller 109 may cause the pump 104 to turn on, or activate one or more power elements 123 operably connected with the device 105. The specified amount of the liquid drug 125 may be determined as an appropriate amount of insulin to drive the measured BG level of the user to the desired BG level. Based on operation of the pump 104, as determined by the control signal 119, the patient 103 may receive the liquid drug from the reservoir 126. The system 100 may operate as a closed-loop system, an open-loop system, or as a hybrid system. In an exemplary closed-loop system, the controller 109 may direct operation of the device 105 without input from the controller 102, and may receive BG level signal 112 from the sensor 108. The sensor 108 may be housed within the device 105 or may be housed in a separate device and communicate wirelessly directly with the device 105.

As further shown, the system 100 may include a needle deployment component 128 that is in communication with the controller 102 or the controller 109. The needle deployment component 128 may include a needle/cannula 129 deployable into the patient 103 and may have one or more holes at a distal end thereof. The needle deployment component 128 may be housed within the device 105 or a separate component connectable to the device 105. The device 105 may be connected to the needle/cannula 129 by a fluid path component 130. The fluid path component 130 may be of any size and shape and may be made from any material. The fluid path component 130 can allow fluid, such as the liquid drug 125 in the reservoir 126, to be transferred to the needle/cannula 129.

The controller 102/109 may be implemented in hardware, software, or any combination thereof. The controller 102/109 may, for example, be a processor, a logic circuit or a microcontroller coupled to a memory. The controller 102/109 may maintain a date and time as well as other functions (e.g., calculations or the like) performed by processors. The controller 102/109 may be operable to execute an artificial pancreas (AP) algorithm stored in memory (not shown) that enables the controller 102/109 to direct operation of the pump 104. For example, the controller 102/109 may be operable to receive an input from the sensor 108, wherein the input indicates an automated insulin delivery (AID) application setting. Based on the AID application setting, the controller 102/109 may modify the behavior of the pump 104 and resulting amount of the liquid drug 125 to be delivered to the patient 103 via the device 105.

In some embodiments, the sensor 108 may be, for example, a continuous glucose monitor (CGM). The sensor 108 may be physically separate from the pump 104, or may be an integrated component within a same housing thereof or otherwise physically integrated. The sensor 108 may provide the controller 102 with data indicative of measured or detected blood glucose levels of the user.

The power element 123 may be a battery, a piezoelectric device, or the like, for supplying electrical power to the device 105. In other embodiments, the power element 123, or an additional power source (not shown), may also supply power to other components of the pump 104, such as the controller 102, memory, the sensor 108, and/or the needle deployment component 128.

In an example, the sensor 108 may be a device communicatively coupled to the controller 102 and may be operable to measure a blood glucose value at a predetermined time interval, such as approximately every 5 minutes, 10 minutes, or the like. The sensor 108 may provide a number of blood glucose measurement values to the AP application.

In some embodiments, the pump 104, when operating in a normal mode of operation, provides insulin stored in the reservoir 126 to the patient 103 based on information (e.g., blood glucose measurement values, target blood glucose values, insulin on board, prior insulin deliveries, time of day, day of the week, inputs from an inertial measurement unit, global positioning system-enabled devices, Wi-Fi-enabled devices, or the like) provided by the sensor 108 or other functional elements of the pump 104. For example, the pump 104 may contain analog and/or digital circuitry that may be implemented as the controller 102/109 for controlling the delivery of the drug or therapeutic agent. The circuitry used to implement the controller 102/109 may include discrete, specialized logic and/or components, an application-specific integrated circuit, a microcontroller or processor that executes software instructions, firmware, programming instructions or programming code enabling, for example, an AP application stored in memory, or any combination thereof. For example, the controller 102/109 may execute a control algorithm and other programming code that may make the controller 102/109 operable to cause the pump to deliver doses of the drug or therapeutic agent to a user at predetermined intervals or as needed to bring blood glucose measurement values to a target blood glucose value. The size and/or timing of the doses may be at least partially pre-programmed, for example, into the AP application by the patient 103 or by a third party (such as a health care provider, a parent or guardian, a manufacturer of the wearable drug delivery device, or the like) using a wired or wireless link.

Although not shown, in some embodiments, the sensor 108 may include a processor, memory, a sensing or measuring device, and a communication device. The memory may store an instance of an AP application as well as other programming code and be operable to store data related to the AP application.

In various embodiments, the sensing/measuring device of the sensor 108 may include one or more sensing elements, such as a blood glucose measurement element, a blood pressure monitor, a heart rate monitor, a blood oxygen sensor element, or the like. The sensor processor may include discrete, specialized logic and/or components, an application-specific integrated circuit, a microcontroller or processor that executes software instructions, firmware, programming instructions stored in memory, or any combination thereof.

Figure 2:
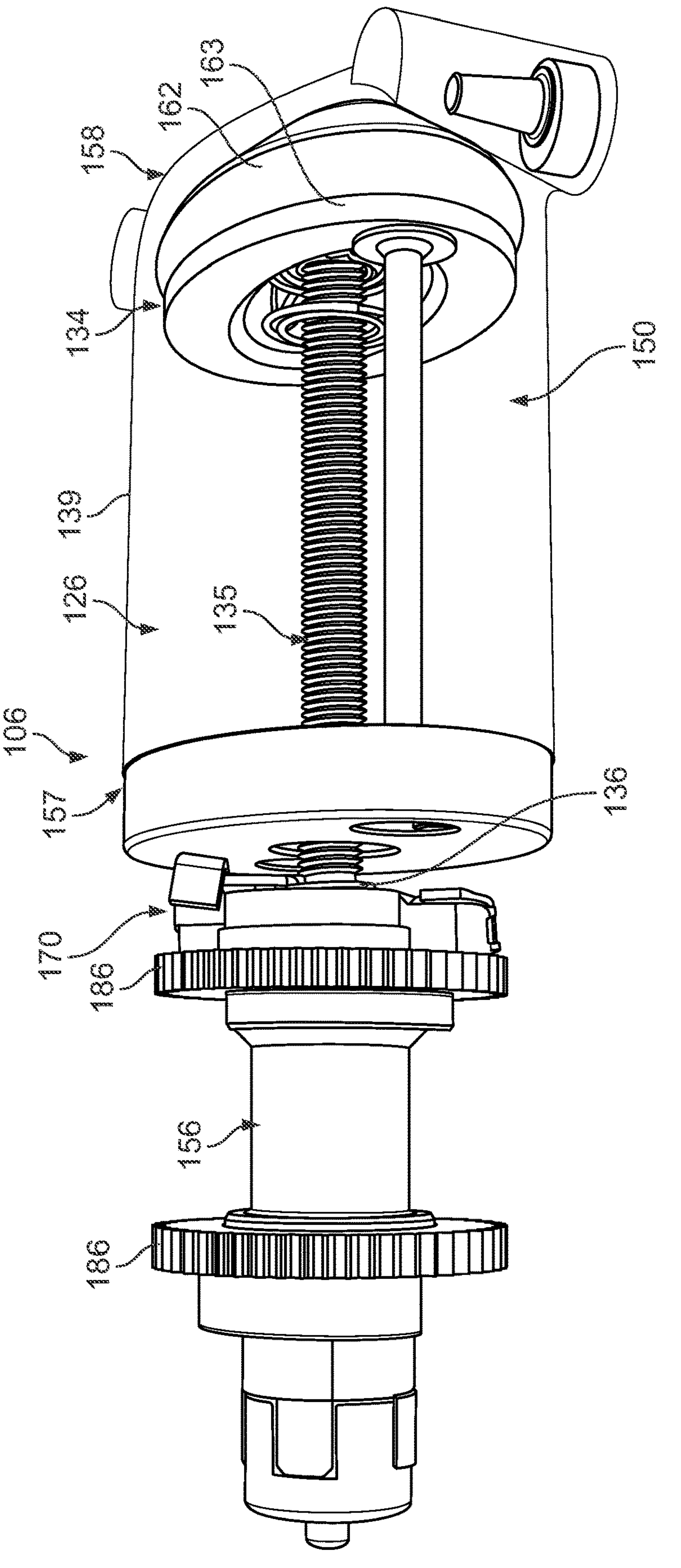
FIG. 2 illustrates a perspective view of a drive mechanism of a delivery pump device, according to embodiments of the present disclosure.

Turning now to FIG. 2, the drive mechanism 106 according to embodiments of the present disclosure will be described in greater detail. As shown, the drive mechanism 106 may be positioned within an interior chamber 150 of the housing 139 of the reservoir 126. The housing 139 may include an outer wall defining the interior chamber 150, wherein the outer wall includes an exterior surface opposite an interior surface. Although non-limiting, the housing 139 may be a circular or an oval-shaped cylinder including a first end 157 opposite a second end 158.

As further shown, the drive mechanism 106 may include the plunger 134 disposed within the interior chamber 150 of the housing 139. In some embodiments, the plunger 134 may include a sealing ring 162 (e.g., O-ring) extending circumferentially about an outer surface 163 of the plunger 134. The sealing ring 162 may be in contact with the interior surface of the outer wall of the housing 139 to create a liquid-tight seal therebetween. The leadscrew 135 may be coupled to the plunger 134, or may be an inseparable, insert-molded assembly.

Some embodiments of the drive mechanism 106 may include a clutch mechanism 170 to facilitate filling and dispensing of fluid within the reservoir 126 and engagement of the drive mechanism 106 for driving fluid out of the reservoir 126. The clutch spring 136 may engage the leadscrew 135 and may be driven by a drive wheel 156 via the clutch mechanism 170.

When the reservoir 126 is empty or in a pre-filled state, as shown in FIG. 2, the plunger 134 is positioned at the second end 158 end of the reservoir 126 such that the plunger 134 is extended and the clutch mechanism 170 is disengaged. In certain embodiments, the reservoir 126 may then be filled with fluid medicament, such as insulin, by opening an inlet port to the reservoir 126 and pumping in the insulin under sufficient hydraulic pressure to retract the plunger 134 within the reservoir 126 toward the first end 157. Thereafter, the inlet port may be closed. When the reservoir 126 is filled and the plunger 134 has moved to or toward the first end 157 of the reservoir 126, the clutch mechanism 170 remains disengaged to allow the leadscrew 135 to pass through the clutch spring and the into an elongated cylindrical bore (along the drive axis) of a hub of the drive wheel 156. The clutch mechanism 170 may then be engaged such that rotation of the drive wheel 156 causes the clutch mechanism 170 to rotate the clutch spring 136, which causes the leadscrew 135 to advance the plunger 134 into the reservoir 126 to deliver the fluid therefrom. In alternative embodiments, the reservoir 126 may be filled when the plunger 134 is already retracted. In the illustrated embodiment, the drive wheel 156 may include one or more ratchets 186 that are engaged by an actuator to incrementally drive the drive wheel 156 and advance the plunger 134 across the reservoir 126.

Figure 3A:
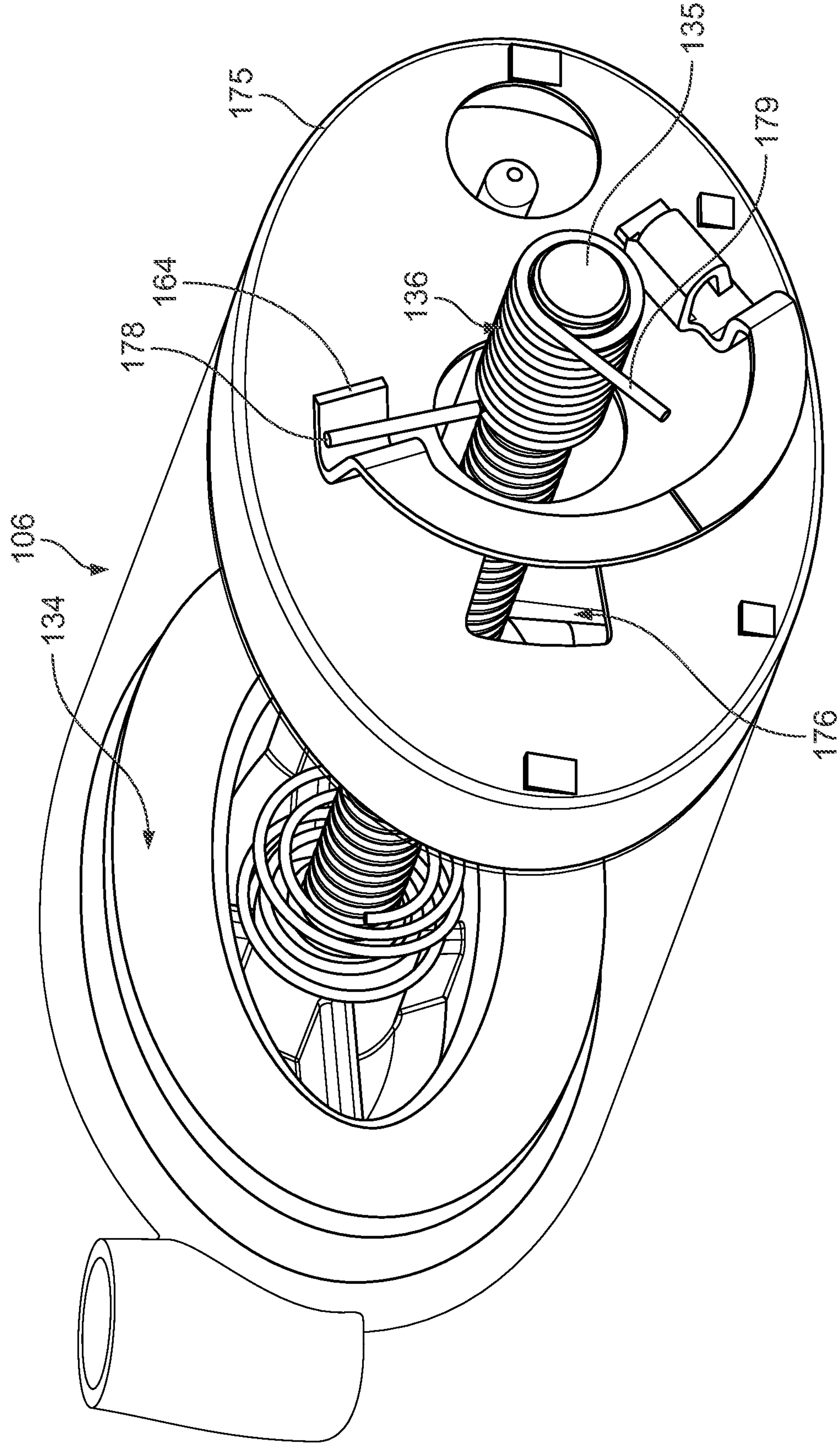
FIG. 3A illustrates a perspective view of a portion of the drive mechanism of FIG. 2, according to embodiments of the present disclosure.
Figure 3B:
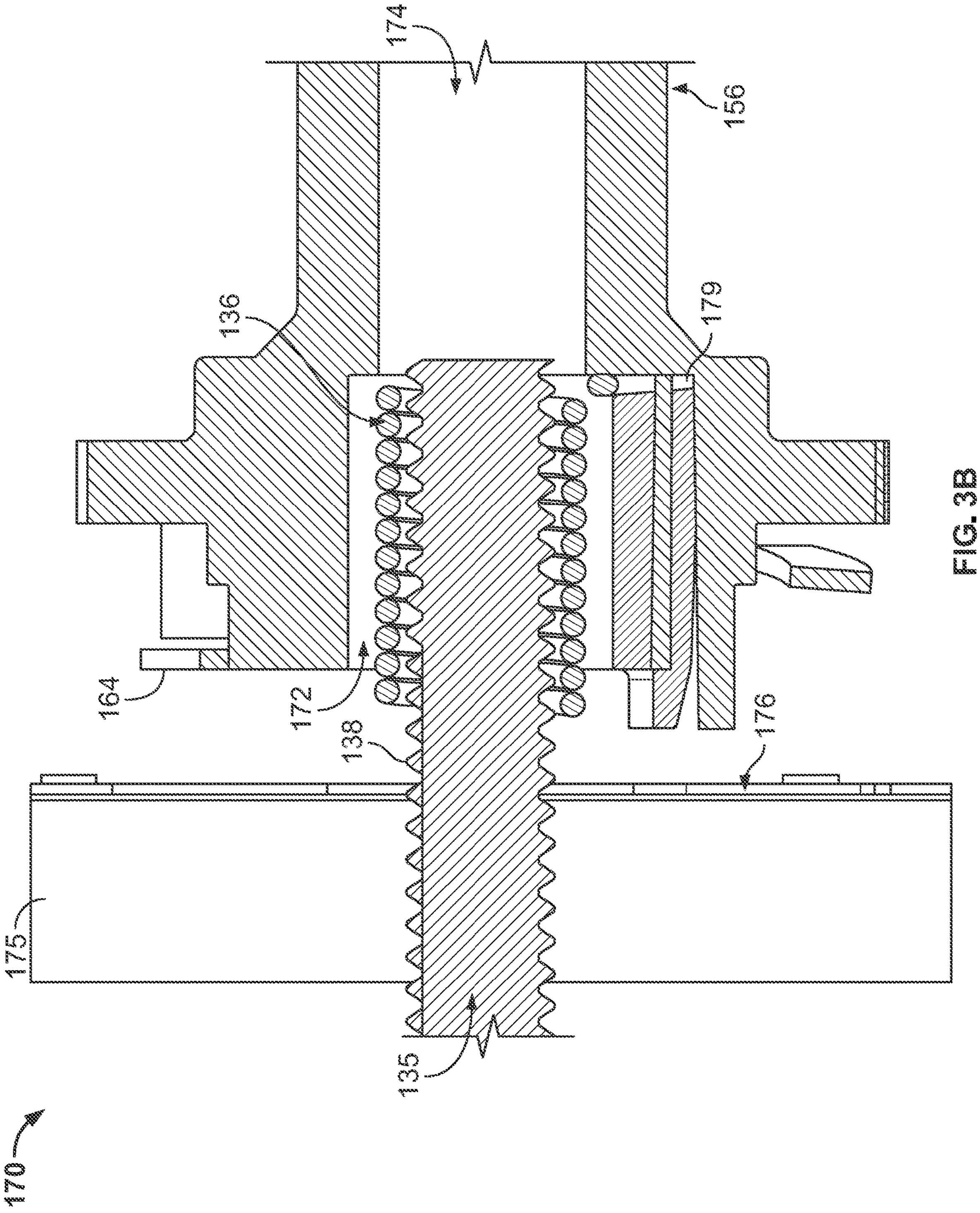
FIG. 3B is a side cross-sectional view illustrating a portion of the drive mechanism, according to embodiments of the present disclosure.

In some embodiments, as illustrated in FIGS. 3A-3B, the clutch spring 136 of the clutch mechanism 170 may be a helical torsion spring located in a counterbore 172 (FIG. 3B) at one end of the drive wheel 156. The ID of the clutch spring 136 may be larger than the outside diameter of the leadscrew 135 when the clutch spring 136 is loaded, thereby disengaging the clutch spring 136 from the leadscrew 135 and allowing the leadscrew 135 to pass through a center aperture of the clutch spring 136 and into an elongated bore 174 of the drive wheel 156. Alternatively, the ID of the clutch spring 136 may be smaller than the outside diameter of the leadscrew 135 when the clutch spring 136 is unloaded, thereby engaging or gripping the leadscrew 135 and allowing the drive wheel 156 to rotate the leadscrew 135. In some embodiments, the clutch spring 136 engages external threading 138 of the leadscrew 135.

In the illustrated embodiment, prior to filing the reservoir 126, the clutch spring 136 may be held in the loaded, disengaged position by a spring latch 164 engaged with the drive wheel 156. After the reservoir 126 has been filled, the clutch spring 136 may be engaged by rotating the drive wheel 156 until the spring latch 164 releases the clutch spring 136, allowing the clutch spring 136 to unload and grip leadscrew 135. The fluid may then be dispensed from the reservoir 126 with continued rotation of the drive wheel 156.

In some embodiments, the spring latch 164 may be biased by the clutch spring 136 such that as the drive wheel 156 rotates, the spring latch 164 moves rotationally against a surface of a reservoir cap 175 until the clutch spring 136 deflects the spring latch 164 into a window 176 in the reservoir cap 175. When the spring latch 164 moves into the window 176, a first end 178 (FIG. 3A) of the clutch spring 136 held by the spring latch 164 is released, thus engaging the clutch mechanism 170. When the clutch spring 136 is engaged, the drive wheel 156 contacts a second end 179 of the clutch spring 136 to create a thrust on the clutch spring 136 that causes the clutch spring 136 to rotate the leadscrew 135.

Figure 4A:
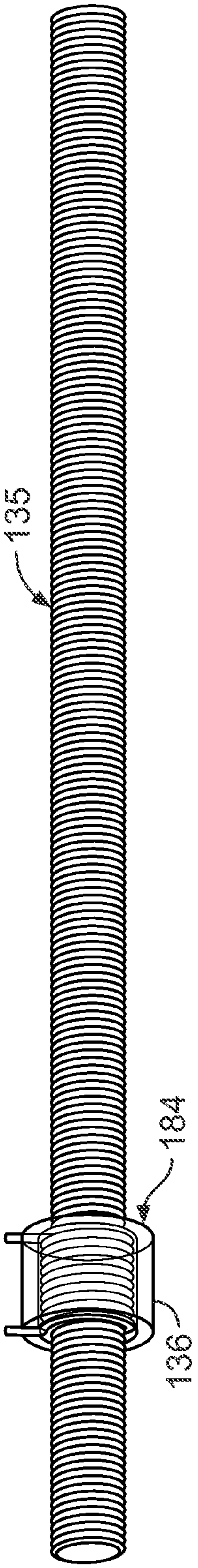
FIGS. 4A-4B illustrate perspective views of a leadscrew and a clutch spring of the drive mechanism, according to embodiments of the present disclosure.
Figure 4B:
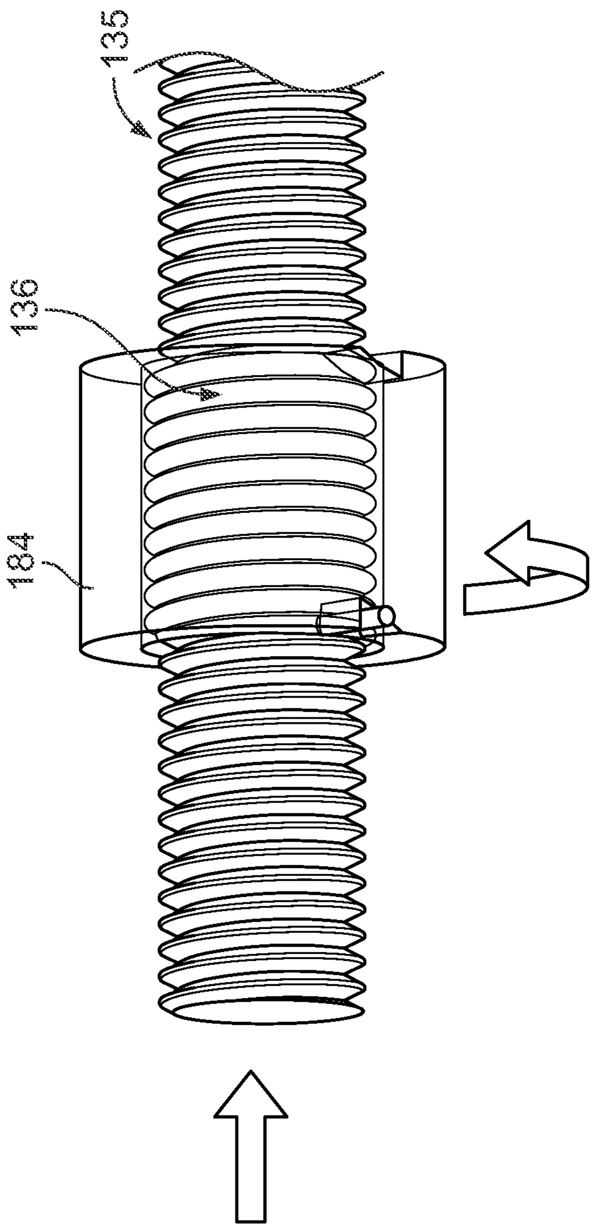

Turning now to FIGS. 4A-4B, operation of the clutch spring 136 and leadscrew 135 according to another embodiment will be described. In this embodiment, the clutch spring 136 may be coupled to, or extend along, an interior surface of a slider 184. The slider 184 may be a cylinder coupled to the plunger (not shown). This embodiment may reduce the required length of the overall drive system (and the clutch mechanism in particular) to approximately half, thus enabling the overall size of the drive mechanism to be reduced. In addition, no tube nut is required in this drive mechanism, which reduces the overall part count and complexity of the system. In other prior drive mechanisms, a tube nut was positioned between a spring and the leadscrew and was used to convert the rotational motion of a rotating drive member to translational motion of the lead screw. Such tube nuts typically extended along much of the length of the leadscrew, thereby increasing the required length of the clutch mechanism and overall drive system to approximately 2× the length of the leadscrew, and also allowed the drive member to rotate the leadscrew via two components, i.e., a spring and the tube nut. In the advances disclosed herein, the tube nut is removed and the spring is modified to allow the spring to engage directly with the leadscrew. As explained above, this reduces the required length of the overall drive system, overcoming the "2× length" problem, while also reducing the number of required parts for the drive system and clutch mechanism.

As described above, the clutch spring 136 may initially be in the loaded configuration with an ID larger than the OD of the leadscrew 135, allowing the slider 184 to move freely along the leadscrew 135 as the reservoir is being filled. When released, the clutch spring 136 causes a reduction in the ID of the clutch spring 136 and engagement of the clutch spring 136 and the slider 184 with the leadscrew 135. After release of the clutch spring 136, the slider 184 functions similar to a drive nut, while the clutch spring 136 acts as internal threading engaged with and/or following the threads on the OD of the leadscrew 135. Hence, rotation of the clutch spring 136 results in the linear motion of the leadscrew 135 and the plunger, enabling the drive mechanism to accurately dispense fluid from the reservoir.

Figure 5A:
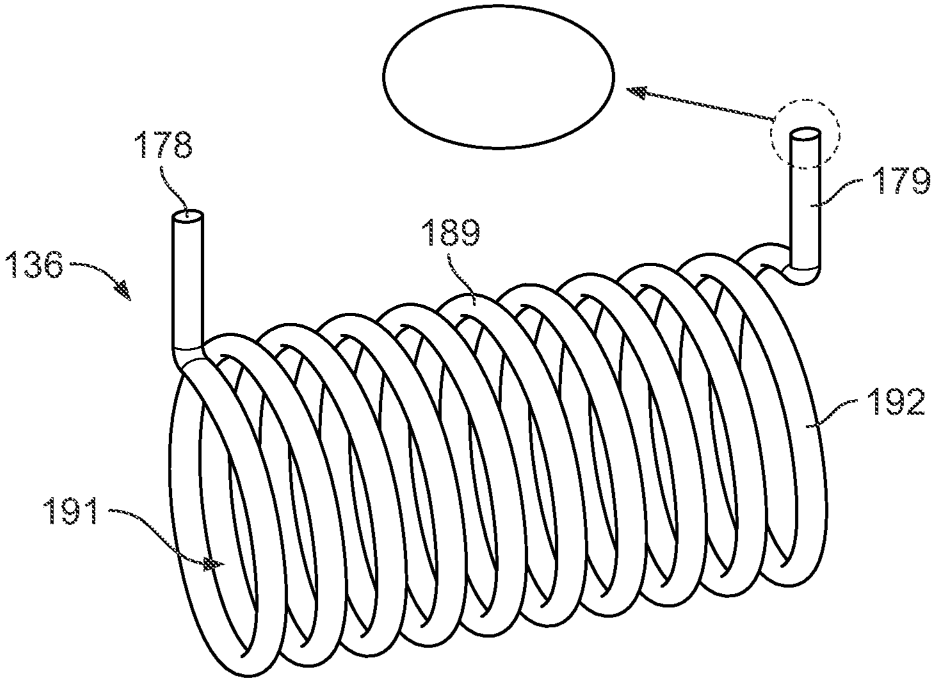
FIGS. 5A-5C are perspective views illustrating various clutch springs, according to embodiments of the present disclosure.
Figure 5B:
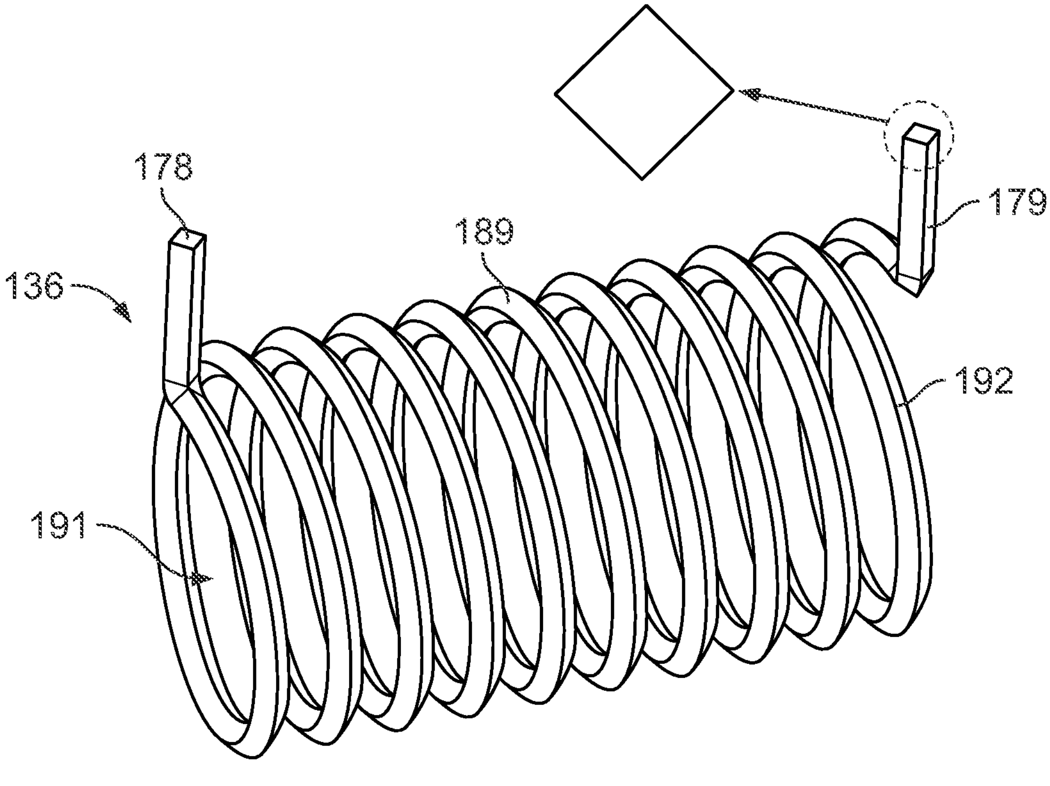
Figure 5C:
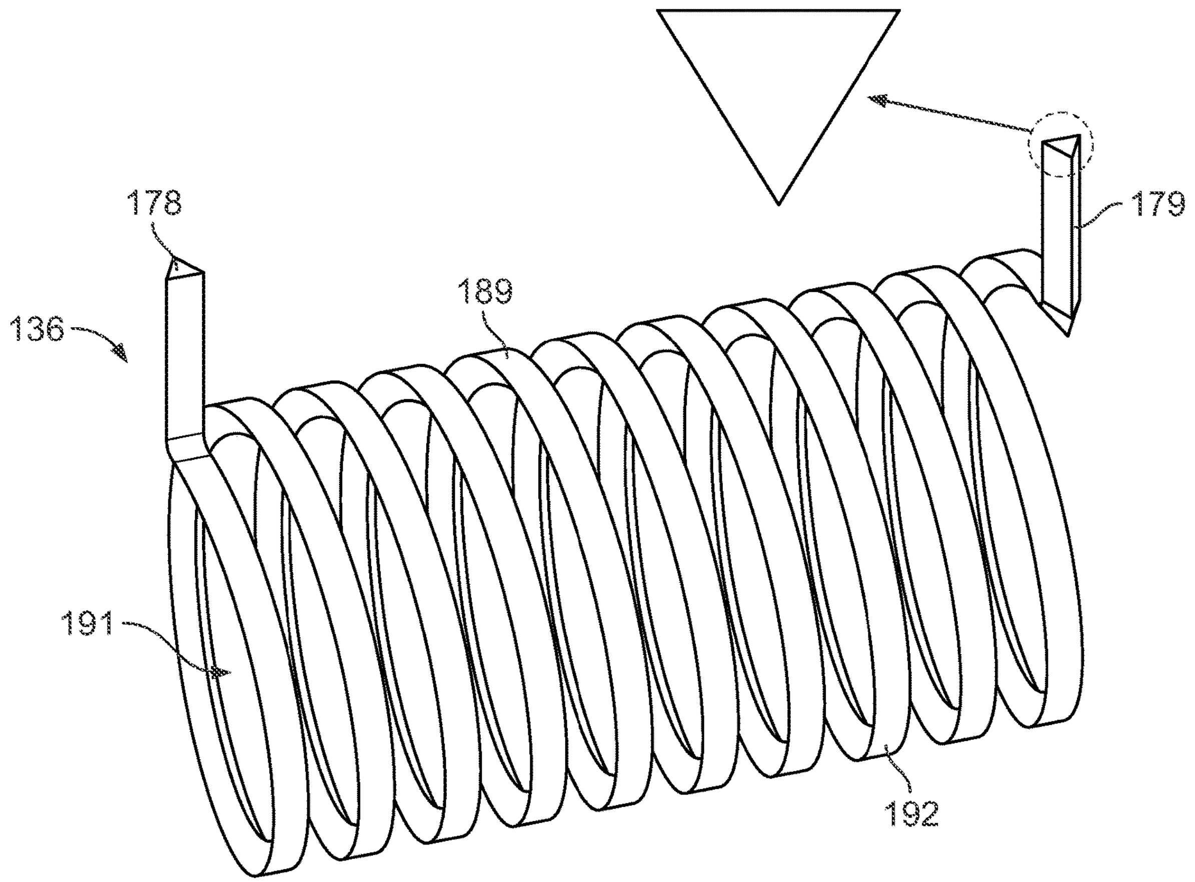

FIGS. 5A-5C demonstrate various non-limiting examples of the clutch spring 136 described herein. As shown, each clutch spring 136 may include a helically shaped main body 189 between the first end 178 and the second end 179. The main body 189 may define a center aperture 191 operable to receive the leadscrew therein. The main body 189 may include a plurality of loops or convolutions 192 operable to engage indentations of the external threading of the leadscrew. Although non-limiting, the clutch spring 136 may have a circular cross-section, an oval or elliptical cross-section (FIG. 5A), a square or diamond profile (FIG. 5B), or a triangular profile (FIG. 5C). The non-circular profiles can be used to create a complimentary, mating thread-form geometry with the external threading of the lead screw 135.

Figure 6:
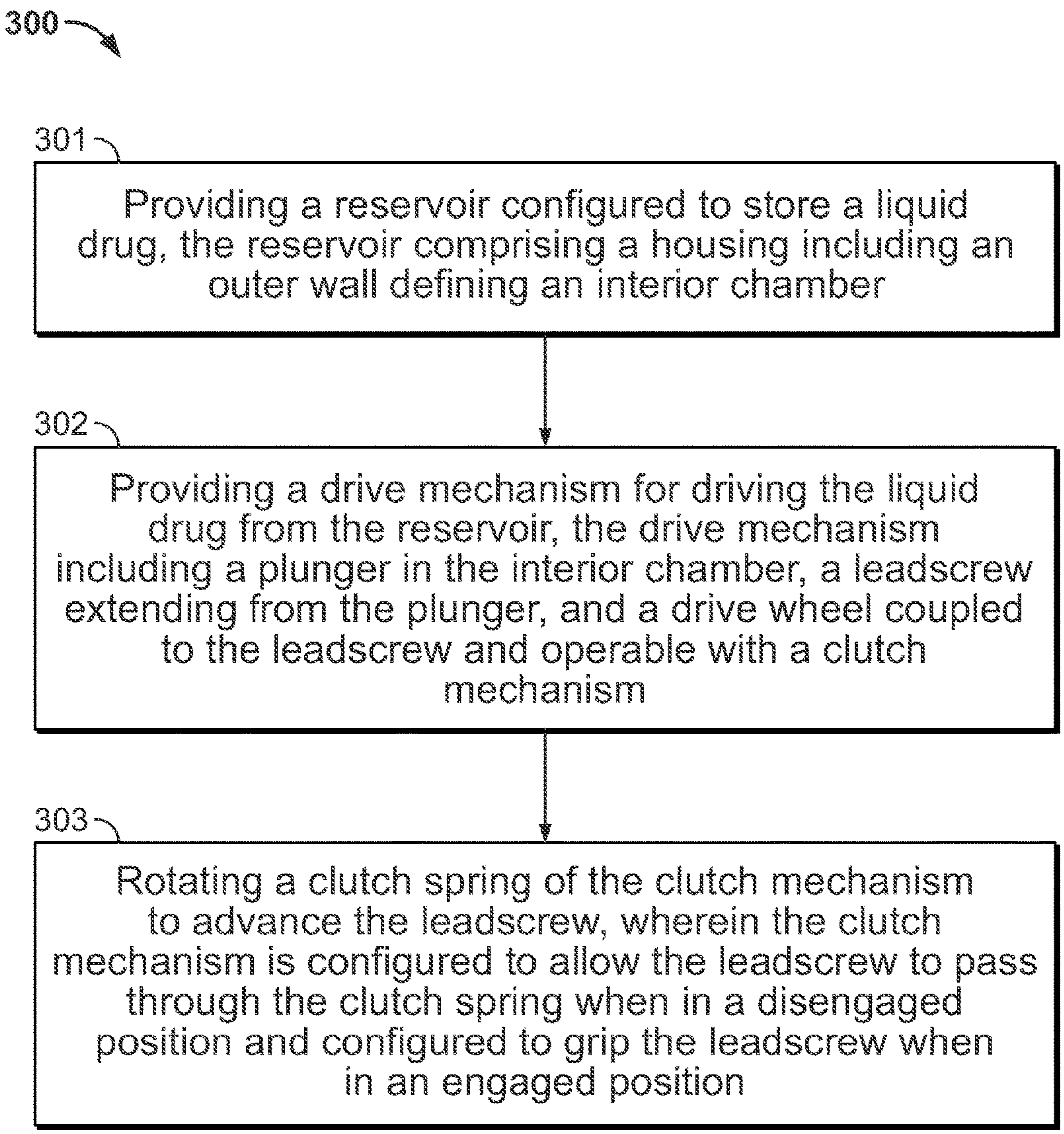
FIG. 6 illustrates a process flow of a method according to embodiments of the present disclosure.

FIG. 6 illustrates an example process 300 according to embodiments of the present disclosure. At block 301, the process 300 may include providing a reservoir configured to store a liquid drug, the reservoir comprising a housing including an outer wall defining an interior chamber.

At block 302, the process 300 may include providing a drive mechanism for driving the liquid drug from the reservoir. In some embodiments, the drive mechanism may include a plunger received in the interior chamber of the reservoir, a leadscrew extending from the plunger, and a drive wheel coupled to the leadscrew and operable with a clutch mechanism. The plunger may create a seal against an interior surface of the outer wall of the housing.

At block 303, the process 300 may further include rotating a clutch spring of the clutch mechanism to advance the leadscrew, wherein the clutch mechanism is configured to allow the leadscrew to pass through the clutch spring when in a disengaged position and is configured to grip the leadscrew when in an engaged position. In some embodiments, the process 300 may further include rotating the drive wheel to rotate the clutch spring to advance the leadscrew and the plunger into the reservoir. In some embodiments, the clutch spring may be provided in direct physical contact with an exterior of the leadscrew when the clutch mechanism is engaged with the leadscrew. In some embodiments, rotating the drive wheel causes the plunger to dispense the fluid from the reservoir.

In some embodiments, the process 300 may include engaging and disengaging the clutch spring with a spring latch. In some embodiments, the clutch mechanism may be released from the disengaged position by releasing the clutch spring from the spring latch by rotating the drive wheel.

As used herein, the algorithms or computer applications that manage blood glucose levels and insulin therapy may be referred to as an "artificial pancreas" algorithm-based system, or more generally, an artificial pancreas (AP) application. An AP application may be programming code stored in a memory device and that is executable by a processor, controller or computer device.

The techniques described herein for a drug delivery system (e.g., the system 100 or any components thereof) may be implemented in hardware, software, or any combination thereof. Any component as described herein may be implemented in hardware, software, or any combination thereof. For example, the system 100 or any components thereof may be implemented in hardware, software, or any combination thereof. Software related implementations of the techniques described herein may include, but are not limited to, firmware, application specific software, or any other type of computer readable instructions that may be executed by one or more processors. Hardware related implementations of the techniques described herein may include, but are not limited to, integrated circuits (ICs), application specific ICs (ASICs), field programmable arrays (FPGAs), and/or programmable logic devices (PLDs). In some examples, the techniques described herein, and/or any system or constituent component described herein may be implemented with a processor executing computer readable instructions stored on one or more memory components.

Some examples of the disclosed devices may be implemented, for example, using a storage medium, a computer-readable medium, or an article of manufacture which may store an instruction or a set of instructions that, if executed by a machine (i.e., processor or controller), may cause the machine to perform a method and/or operation in accordance with examples of the disclosure. Such a machine may include, for example, any suitable processing platform, computing platform, computing device, processing device, computing system, processing system, computer, processor, or the like, and may be implemented using any suitable combination of hardware and/or software. The computer-readable medium or article may include, for example, any suitable type of memory unit, memory, memory article, memory medium, storage device, storage article, storage medium and/or storage unit, for example, memory (including non-transitory memory), removable or non-removable media, erasable or non-erasable media, writeable or re-writeable media, digital or analog media, hard disk, floppy disk, Compact Disk Read Only Memory (CD-ROM), Compact Disk Recordable (CD-R), Compact Disk Rewriteable (CD-RW), optical disk, magnetic media, magneto-optical media, removable memory cards or disks, various types of Digital Versatile Disk (DVD), a tape, a cassette, or the like. The instructions may include any suitable type of code, such as source code, compiled code, interpreted code, executable code, static code, dynamic code, encrypted code, programming code, and the like, implemented using any suitable high-level, low-level, object-oriented, visual, compiled and/or interpreted programming language. The non-transitory computer readable medium embodied programming code may cause a processor when executing the programming code to perform functions, such as those described herein.

Certain examples of the present disclosed subject matter were described above. It is, however, expressly noted that the present disclosed subject matter is not limited to those examples, but rather the intention is that additions and modifications to what was expressly described herein are also included within the scope of the disclosed subject matter. Moreover, it is to be understood that the features of the various examples described herein were not mutually exclusive and may exist in various combinations and permutations, even if such combinations or permutations were not made express herein, without departing from the spirit and scope of the disclosed subject matter. In fact, variations, modifications, and other implementations of what was described herein will occur to those of ordinary skill in the art without departing from the spirit and the scope of the disclosed subject matter. As such, the disclosed subject matter is not to be defined only by the preceding illustrative description.

Program aspects of the technology may be thought of as "products" or "articles of manufacture" typically in the form of executable code and/or associated data that is carried on or embodied in a type of machine readable medium. Storage type media include any or all of the tangible memory of the computers, processors or the like, or associated modules thereof, such as various semiconductor memories, tape drives, disk drives and the like, which may provide non-transitory storage at any time for the software programming. It is emphasized that the Abstract of the Disclosure is provided to allow a reader to quickly ascertain the nature of the technical disclosure. It is submitted with the understanding that it will not be used to interpret or limit the scope or meaning of the claims. In addition, in the foregoing Detailed Description, various features are grouped together in a single example for streamlining the disclosure. This method of disclosure is not to be interpreted as reflecting an intention that the claimed examples require more features than are expressly recited in each claim. Rather, as the following claims reflect, inventive subject matter lies in less than all features of a single disclosed example. Thus, the following claims are hereby incorporated into the Detailed Description, with each claim standing on its own as a separate example. In the appended claims, the terms "including" and "in which" are used as the plain-English equivalents of the respective terms "comprising" and "wherein," respectively. Moreover, the terms "first," "second," "third," and so forth, are used merely as labels and are not intended to impose numerical requirements on their objects.

The foregoing description of example examples has been presented for the purposes of illustration and description. It is not intended to be exhaustive or to limit the present disclosure to the precise forms disclosed. Many modifications and variations are possible in light of this disclosure. It is intended that the scope of the present disclosure be limited not by this detailed description, but rather by the claims appended hereto. Future filed applications claiming priority to this application may claim the disclosed subject matter in a different manner and may generally include any set of one or more limitations as variously disclosed or otherwise demonstrated herein.

What is claimed is:

1. A wearable drug delivery device, comprising:
- a reservoir configured to store a fluid, the reservoir comprising a housing defining an interior chamber;
- a drive mechanism for driving the fluid from the reservoir, the drive mechanism comprising:
  - a plunger in the interior chamber of the reservoir;
  - a leadscrew extending from the plunger; and
  - a clutch mechanism engaged with the leadscrew, wherein the clutch mechanism is configured to allow the leadscrew to pass through the clutch mechanism when disengaged and configured to directly grip the leadscrew when engaged such that the clutch mechanism rotates to advance the leadscrew and the plunger in the reservoir.

2. The wearable drug delivery device of claim 1, wherein the clutch mechanism comprises a clutch spring, and wherein the clutch spring is in direct physical contact with an exterior of the leadscrew when the clutch mechanism is engaged with the leadscrew.

3. The wearable drug delivery device of claim 2, wherein the clutch mechanism further includes a spring latch operable to hold the clutch spring in a disengaged position and configured to release the clutch spring such that the clutch spring moves to an engaged position.

4. The wearable drug delivery device of claim 3, wherein the spring latch is operable to release the clutch spring in response to movement of the drive wheel.

5. The wearable drug delivery device of claim 2, further comprising a slider connected with the clutch spring.

6. The wearable drug delivery device of claim 5, wherein the clutch spring is provided along an interior of the slider.

7. The wearable drug delivery device of claim 2, wherein the clutch spring has a square profile, a triangular profile, or an elliptical profile.

8. The wearable drug delivery device of claim 1, further comprising a drive wheel, wherein the drive wheel is operable with the clutch mechanism to rotate and advance the leadscrew.

9. A wearable drug delivery device, comprising:

a reservoir configured to store a liquid drug, the reservoir comprising a housing including an outer wall defining an interior chamber;

a drive mechanism for driving the liquid drug from the reservoir, the drive mechanism comprising:

a plunger in the interior chamber of the reservoir;

a leadscrew extending from the plunger; and a drive wheel operable with a clutch mechanism to rotate a clutch spring to advance the leadscrew, wherein the clutch mechanism is configured to allow the leadscrew to pass through the clutch spring when in a disengaged position and configured to directly grip the leadscrew by the clutch spring when in an engaged position such that the drive wheel rotates the clutch spring to advance the leadscrew and the plunger into the reservoir.

10. The wearable drug delivery device of claim 9, wherein the clutch spring is in direct physical contact with an exterior of the leadscrew when the clutch mechanism is in the engaged position.

11. The wearable drug delivery device of claim 9, wherein the clutch mechanism further includes a spring latch operable to engage and disengage the clutch spring.

12. The wearable drug delivery device of claim 11, wherein the spring latch is operable to release the clutch spring in response to movement of the drive wheel.

13. The wearable drug delivery device of claim 9, further comprising a slider connected with the clutch spring, wherein the clutch spring is provided along an interior of the slider.

14. The wearable drug delivery device of claim 9, wherein the clutch spring has a square profile, a triangular profile, a circular profile, or an elliptical profile.

15. A method comprising:

providing a reservoir configured to store a liquid drug, the reservoir comprising a housing defining an interior chamber;

providing a drive mechanism for driving the liquid drug from the reservoir, the drive mechanism comprising:

a plunger in the interior chamber of the reservoir;

a leadscrew extending from the plunger; and a drive wheel operable with a clutch mechanism, wherein the clutch mechanism is coupled to the leadscrew; and rotating a clutch spring of the clutch mechanism to advance the leadscrew, wherein the clutch mechanism is configured to allow the leadscrew to pass through the clutch spring when in a disengaged position and is configured to directly grip the leadscrew by the clutch spring when in an engaged position.

16. The method of claim 15, further comprising rotating the drive wheel to rotate the clutch spring to advance the leadscrew and the plunger into the reservoir.

17. The method of claim 15, further comprising providing the clutch spring in direct physical contact with an exterior of the leadscrew when the clutch mechanism is in the engaged position.

18. The method of claim 15, further comprising engaging and disengaging the clutch spring with a spring latch.

19. The method of claim 15, further comprising releasing the clutch mechanism from the disengaged position further comprises releasing the clutch spring from the spring latch by rotating the drive wheel.

20. The method of claim 15 further comprising rotating the drive wheel to dispense the fluid from the reservoir.

* * * * *